United States Patent [19]

Staendeke

[11] Patent Number: 5,391,698
[45] Date of Patent: Feb. 21, 1995

[54] PHOSPHORIC ACID POLYESTERS AND A PROCESS FOR THEIR PREPARATION

[75] Inventor: Horst Staendeke, Lohmar, Germany

[73] Assignee: Hoechst Aktiengesellschaft, Frankfurt am Main, Germany

[21] Appl. No.: 187,406

[22] Filed: Jan. 25, 1994

[30] Foreign Application Priority Data

Feb. 9, 1993 [DE] Germany .................. 4303654

[51] Int. Cl.$^6$ .................................. C08G 63/692
[52] U.S. Cl. ......................... 528/287; 528/279; 528/289; 528/368; 528/398; 528/411; 528/418; 528/423
[58] Field of Search ............... 528/279, 287, 289, 291, 528/368, 398, 411, 418, 423, 220

[56] References Cited

U.S. PATENT DOCUMENTS 4,096,114  6/1978  Minagawa et al. .............. 524/101
4,154,930  5/1979  Halpern ......................... 544/195

FOREIGN PATENT DOCUMENTS 0074090  3/1983  European Pat. Off.
0389430  3/1990  European Pat. Off.

OTHER PUBLICATIONS

Rätz, R., et al., *J. Org. Chem.* 28:1608–1612 (1963).

*Primary Examiner*—Samuel A. Acquah
*Attorney, Agent, or Firm*—Connolly and Hutz

[57] ABSTRACT

The invention relates to phosphoric acid polyesters according to the formulae in which R is $=CH_2$, $=C_2H_4$ or $=C_3H_6$ and m is 1 to 10 and n is 1 to 6.

To prepare these phosphoric acid polyesters, the cyclic phosphoric acid ester 2,4,8,10-tetraoxa-3,9-dioxo-3,9-dihydroxy-phosphaspiro[5.5]-undecane is reacted with tris-hydroxyalkyl cyanurate or tris-hydroxyalkyl isocyanurate at temperatures of 120° to 250° C. in the presence of a catalyst for 2 to 12 hours, while mixing intensively.

18 Claims No Drawings

PHOSPHORIC ACID POLYESTERS AND A PROCESS FOR THEIR PREPARATION

The present invention relates to phosphoric acid polyesters and a process for their preparation.

The dichloride of a cyclic phosphoric acid ester (2,4,8,10-tetraoxa-3,9-dioxo-3,9-dichloro-phosphaspiro-[5.5]-undecane) is accessible in good yields by reaction of pentaerythritol with excess phosphorus oxychloride and can be converted into the cyclic phosphoric acid ester (2,4,8,10-tetraoxa-3,9-dioxo-3,9-dihydroxyphosphaspiro[5.5]-undecane) by subsequent hydrolysis (cf. J. Org. Chem. 28, 1963, pages 1608 to 1612).

These conversions are based on the following reactions:

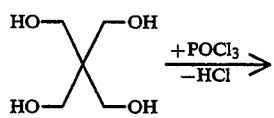

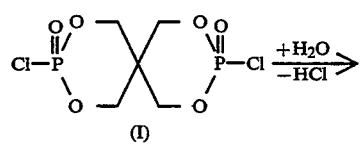

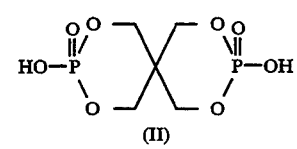

According to the invention, the cyclic phosphoric acid ester (II) thus obtained is then reacted at elevated temperature with a tris-hydroxyalkyl cyanurate of the formula (III)

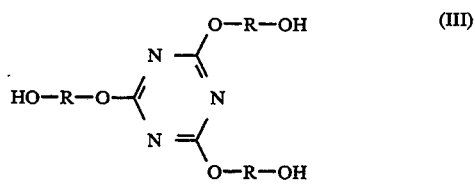

or a tris-hydroxyalkyl isocyanurate of the formula (IV)

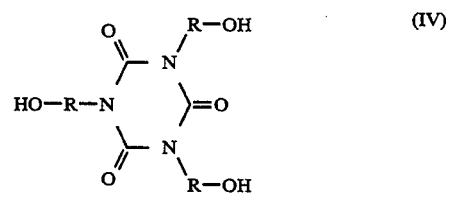

reaction products of the formula (V)

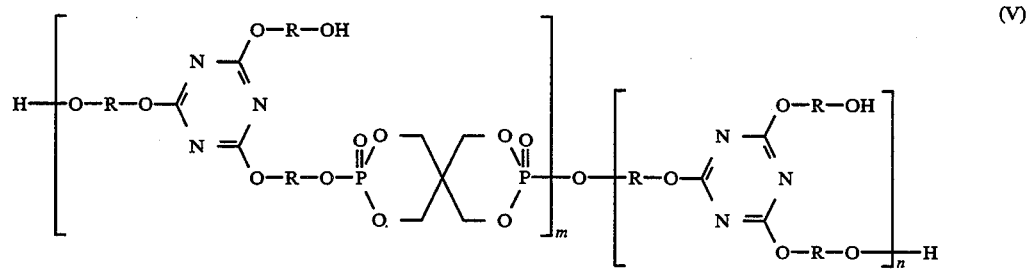

or of the formula (VI)

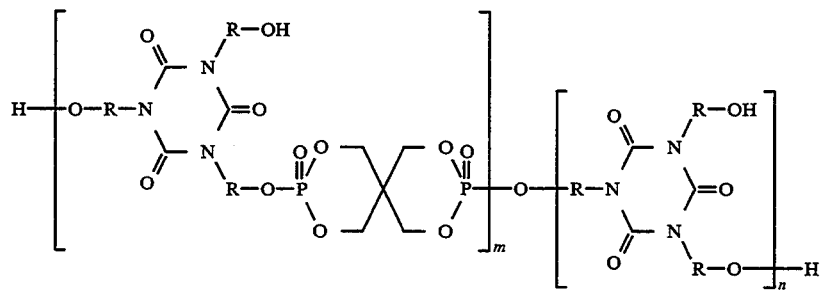

in which R is $=CH_2$, $=C_2H_4$ or $=C_3H_6$ and m is 1 to 10, preferably 1 to 6, and n is 1 to 6, preferably 1 to 3, being formed with water being split off.

To prepare these phosphoric acid polyesters, the cyclic phosphoric acid ester 2,4,8,10-tetraoxa-3,9-dioxo-3,9-dihydroxy-phosphaspiro[5.5]-undecane is reacted with tris-hydroxyalkyl cyanurate or tris-hydroxyalkyl isocyanurate at temperatures of 120° to 250° C. in the presence of a catalyst for 2 to 12 hours, while mixing intensively.

The process mentioned for the preparation of the phosphoric acid polyesters can furthermore optionally also be designed such that a) the reaction is carried out at temperatures of 150° to 200° C.;
b) the reaction is carried out for 5 to 10 hours;
c) the catalyst is at least one organometallic compound;
d) the catalyst contains titanium;

e) tetra-n-butyl titanate is used.

The process for the preparation of the phosphoric acid polyesters according to the invention can be carried out under normal pressure or under reduced pressure.

The phosphoric acid polyesters according to the invention can be used as flameproofing agents, in particular in combination with ammonium polyphosphate.

The percentage data in the following examples are percentages by weight.

EXAMPLE 1

1096 g (4.2 mol) of tris-(2-hydroxyethyl) isocyanurate (THEIC)
1092 g (4.2 mol) of cyclic phosphoric acid ester (2,4,8,10-tetraoxa-3,9-dioxo-3,9-dihydroxy-phosphaspiro[5.5]-undecane)
21 g of tetra-n-butyl titanate
were introduced into a laboratory kneader (operating volume: 5 l) which can be heated and the mixture was reacted under a weak stream of nitrogen in accordance with the following time/temperature program.

| Time (hours) | Temperature (°C.) |
| --- | --- |
| 2 | 20–150 |
| 1 | 150–170 |
| 4 | 170–185 |

After cooling, the reaction product was ground in a porcelain-ball mill and then analyzed:

| Content of | | |
| --- | --- | --- |
| | phosphorus | 10.0% |
| | carbon | 33.5% |
| | nitrogen | 9.0% |
| | water-solubility at 25° C.: | 3.0% |
| | water-solubility at 60° C.: | 3.4% |

If $=C_2H_4$ is inserted for R, 2 for m and 1 for n in the formula (VI) (cf. page 3), the following values can be calculated:

| Content of | | |
| --- | --- | --- |
| | phosphorus | 10.1% |
| | carbon | 36.1% |
| | nitrogen | 10.2% |

These values agree relatively well with the values determined analytically.

EXAMPLE 2

The procedure followed was analogous to Example 1, but
1044 g (4 mol) of THEIC
780 g (3 mol) of cyclic phosphoric acid ester
18 g of tetra-n-butyl titanate
were employed.

The starting substances were reacted in accordance with the following time/temperature program:

| Time (hours) | Temperature (°C.) |
| --- | --- |
| 2 | 20–150 |
| 1 | 150–170 |
| 2 | 170–190 |

The reaction product was worked up analogously to Example 1 and analyzed:

| Content of | | |
| --- | --- | --- |
| | phosphorus | 11.9% |
| | carbon | 32.9% |
| | nitrogen | 8.2% |
| | water-solubility at 25° C.: | 1.7% |
| | water-solubility at 60° C.: | 1.9% |

If $=C_2H_4$ is inserted for R, 8 for m and 1 for n in formula (VI) (cf. page 3), the following values can be calculated:

| Content of | | |
| --- | --- | --- |
| | phosphorus | 12.0% |
| | carbon | 35.1% |
| | nitrogen | 9.1% |

These values agree relatively well with the values determined analytically.

EXAMPLE 3

The procedure followed was analogous to Example 1, but
1305 g (5 mol) of THEIC
650 g (2.5 mol) of cyclic phosphoric acid ester
20 g of tetra-n-butyl titanate
were employed.

The starting substances were reacted in accordance with the following time/temperature program:

| Time (hours) | Temperature (°C.) |
| --- | --- |
| 2 | 20–150 |
| 2 | 150–170 |
| 2 | 170–200 |

The reaction product was worked up analogously to Example 1 and analyzed:

| Content of | | |
| --- | --- | --- |
| | phosphorus | 8.3% |
| | carbon | 36.9% |
| | nitrogen | 11.2% |
| | water-solubility at 25° C.: | 0.4% |
| | water-solubility at 60° C.: | 0.5% |

If $=C_2H_4$ is inserted for R, 1 for m and 1 for n in the formula (VI) (cf. page 3), the following values can be calculated:

| Content of | | |
| --- | --- | --- |
| | phosphorus | 8.3% |
| | carbon | 37.0% |
| | nitrogen | 11.3% |

These values agree virtually entirely with the determined values analytically.

EXAMPLE 4

The procedure followed was analogous to Example 1, but
1305 g (5 mol) of THEIC
520 g (2 mol) of cyclic phosphoric acid ester
18 g of tetra-n-butyl titanate
were employed.

The starting substances were reacted in accordance with the following time/temperature program:

| Time (hours) | Temperature (°C.) |
| --- | --- |
| 2 | 20–150 |
| 2 | 150–170 |
| 6 | 170 to 200 |

The reaction product was worked up analogously to Example 1 and analyzed:

| Content of | phosphorus | 7.1% |
| --- | --- | --- |
| | carbon | 37.8% |
| | nitrogen | 12.0% |
| | water-solubility at 25° C.: | 0.2% |
| | water-solubility at 60° C.: | 0.4% |

If $=C_2H_4$ is inserted for R, 1 for m and 1.5 for n in the formula (VI) (cf. page 3), the following values can be calculated:

| Content of | phosphorus | 7.1% |
| --- | --- | --- |
| | carbon | 38.0% |
| | nitrogen | 12.1% |

These values agree very well with the values determined analytically.

I claim:

1. A phosphoric acid polyester according to the formula

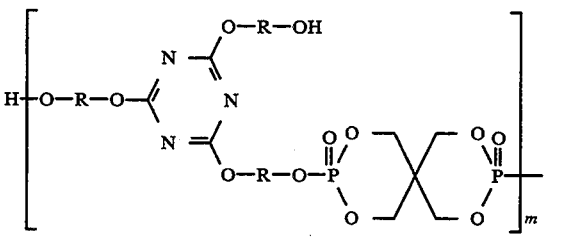

in which R is $=CH_2$, $=C_2H_4$ or $=C_3H_6$ and m is 1 to 10 and n is 1 to 6.

2. A phosphoric acid polyester as claimed in claim 1, wherein m is 1 to 6.

3. A phosphoric acid polyester as claimed in claim 1, wherein n is 1 to 3.

4. A process for the preparation of a phosphoric acid polyester as claimed in claim 1, which comprises reacting the cyclic phosphoric acid ester 2,4,8,10-tetraoxa-3,9-dioxo-3,9-dihydroxyphosphaspiro[5.5]-undecane with tris-hydroxyalkyl cyanurate at temperatures of 120° to 250° C. in the presence of a catalyst for 2 to 12 hours, while mixing intensively.

5. The process as claimed in claim 4, wherein the reaction is carried out at temperatures of 150° to 200° C.

6. The process as claimed in claim 4, wherein the reaction is carried out for 5 to 10 hours.

7. The process as claimed in claim 4, wherein the catalyst is at least one organometallic compound.

8. The process as claimed in claim 7, wherein the catalyst contains titanium.

9. The process as claimed in claim 8, wherein tetra-n-butyl titanate is used.

10. A phosphoric acid polyester according to the formula

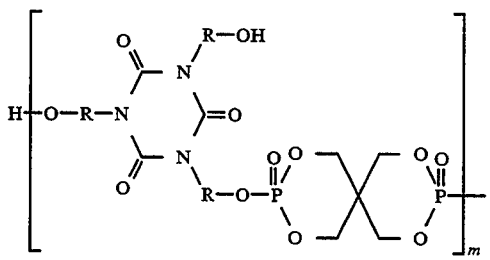

in which R is $=CH_2$, $=C_2H_4$ or $=C_3H_6$ and m is 1 to 10 and n is 1 to 6.

11. A phosphoric acid polyester as claimed in claim 10, wherein m is 1 to 6.

12. A phosphoric acid polyester as claimed in claim 10, wherein n is 1 to 3.

13. A process for the preparation of a phosphoric acid polyester as claimed in claim 10, which comprises reacting the cyclic phosphoric acid ester 2,4,8,10-tetraoxa-3,9-dioxo-3,9-dihydroxyphosphaspiro[5.5]-undecane with tris-hydroxyalkyl isocyanurate at temperatures of 120° to 250° C. in the presence of a catalyst for 2 to 12 hours, while mixing intensively.

14. The process as claimed in claim 13, wherein the reaction is carried out at temperatures of 150° to 200° C.

15. The process as claimed in claim 13, wherein the reaction is carried out for 5 to 10 hours.

16. The process as claimed in claim 13, wherein the catalyst is at least one organometallic compound.

17. The process as claimed in claim 16, wherein the catalyst contains titanium.

18. The process as claimed in claim 17, wherein tetra-n-butyl titanate is used.

* * * * *